(12) United States Patent
Tsao

(10) Patent No.: US 10,159,387 B2
(45) Date of Patent: Dec. 25, 2018

(54) OZONE CLEANING DEVICE

(71) Applicant: Min-Hao Tsao, Taoyuan (TW)

(72) Inventor: Min-Hao Tsao, Taoyuan (TW)

( * ) Notice: Subject to any disclaimer, the term of this patent is extended or adjusted under 35 U.S.C. 154(b) by 353 days.

(21) Appl. No.: 15/063,522

(22) Filed: Mar. 8, 2016

(65) Prior Publication Data
US 2017/0258277 A1 Sep. 14, 2017

(51) Int. Cl.
A47K 7/04 (2006.01)
C01B 13/00 (2006.01)
A61L 2/20 (2006.01)

(52) U.S. Cl.
CPC .............. A47K 7/043 (2013.01); C01B 13/00 (2013.01); A61L 2/202 (2013.01)

(58) Field of Classification Search
CPC ............................ A47L 7/043; A47L 2501/08
See application file for complete search history.

(56) References Cited

PUBLICATIONS https://www.amazon.com/Sharper-Image-Ionic-Clothes-Freshener/dp/B01BURQB7M (Product available from Feb. 17, 2016).*

* cited by examiner

Primary Examiner — Jason Y Ko
(74) Attorney, Agent, or Firm — Leong C. Lei

(57) ABSTRACT

The ozone cleaning device contains an electrically conductive member and a reinforced casing member. The casing member is injection-molded and houses the conductive member inside in an airtight manner. The reinforcement of the casing member, and the tight integration between the casing member and the conductive member jointly achieve enhanced structural strength to prevent the ozone cleaning device from being broken. When the ozone cleaning device is held close to a user and an electrical power is delivered to the conductive member, the conductive member is then conducting to the user and the air in between is influenced by the electrical power to produce ozone for cleaning. The present invention therefore achieves enhanced structural strength, usage safety, and prolonged operational life.

6 Claims, 6 Drawing Sheets

OZONE CLEANING DEVICE

BACKGROUND OF THE INVENTION (a) Technical Field of the Invention

The present invention is generally related to cleaning devices, and more particular to an ozone cleaning device of enhanced structural strength, usage safety, and prolonged operational life.

(b) Description of the Prior Art

As shown in FIG. 1, a conventional ozone cleaning device contains a glass tubular member 91 housing a discharging member 92. A closed and vacuumed space 911 is formed between the tubular member 91 and the discharging member 92. The tubular member 91 is of limited structural strength and, due to the vacuumed space 911, is constantly under external pressure. Therefore, the tubular member 91 is often broken under external impact due to improper storage or usage. In addition to the limited operational life, the ozone cleaning device's operation and transportation require special care. The broken glass could also be harmful to the user.

SUMMARY OF THE INVENTION

Therefore the present invention discloses a novel ozone cleaning device of enhanced structural strength so as to achieve improved usage safety and operational life.

A major objective of the present invention is to reinforce the ozone cleaning device's structural strength to provide convenient and comfortable usage.

Another objective of the present invention is to reinforce the ozone cleaning device's structural strength to prevent various possible damages.

To achieve these objectives, the ozone cleaning device contains an electrically conductive member and a reinforced casing member. The casing member is injection-molded and houses the conductive member inside in an airtight manner. The conductive member is exposed from an end of the casing member and its exposed end is electrically connected a power provision member. The reinforcement of the casing member, and the tight integration between the casing member and the conductive member jointly achieve enhanced structural strength to prevent the ozone cleaning device from being broken. When the ozone cleaning device is held close to a user and an electrical power is delivered to the conductive member, the conductive member is then conducting to the user and the air in between is influenced by the electrical power to produce ozone for cleaning. The present invention therefore achieves enhanced structural strength, usage safety, and prolonged operational life.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
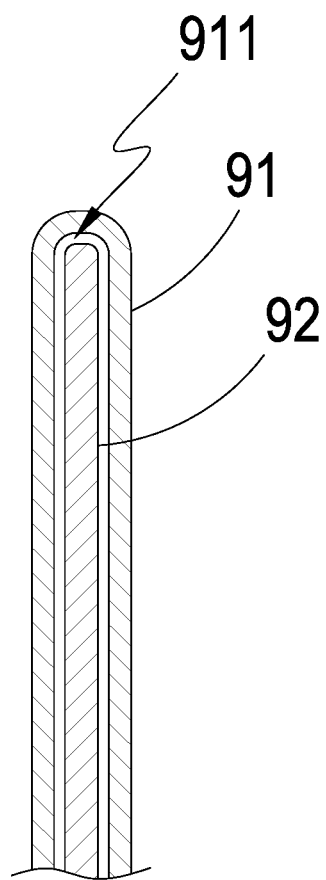
FIG. 1 is a scheme diagram showing the structure of a conventional ozone cleaning device.
Figure 2:
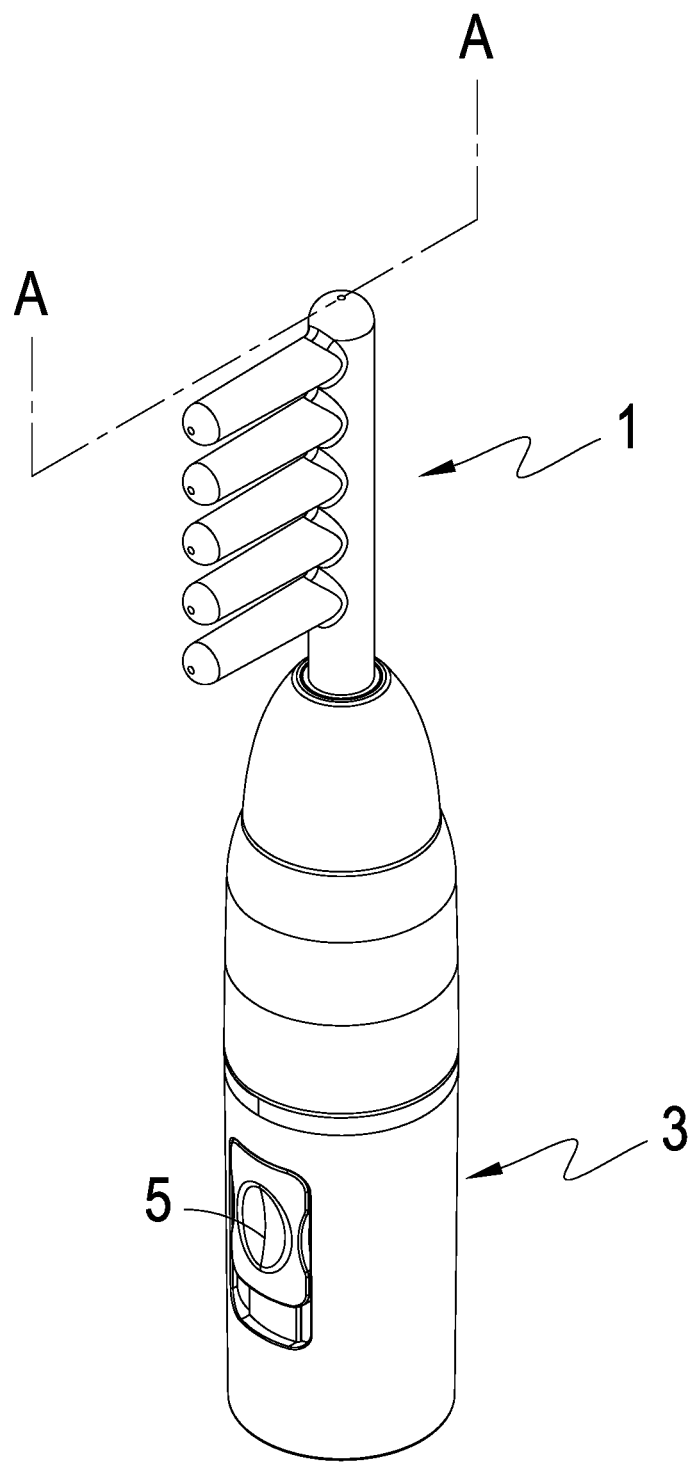
FIG. 2 is a perspective diagram showing an ozone cleaning device according to a first embodiment of the present invention.
Figure 3:
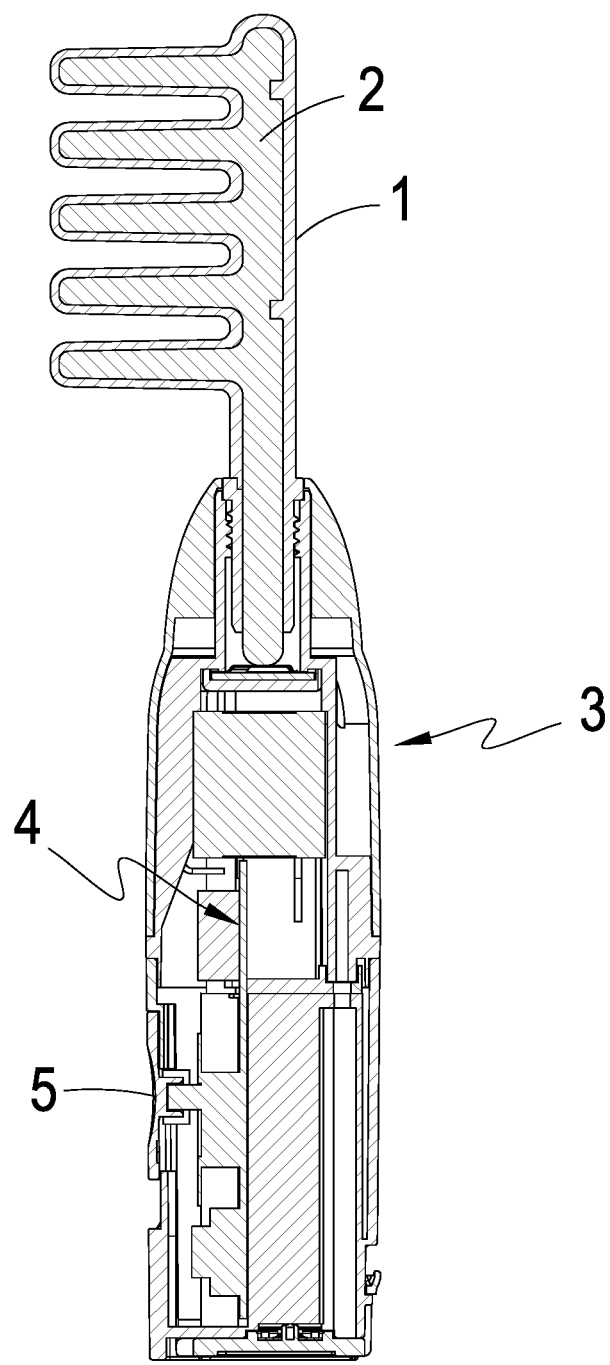
FIG. 3 is a sectional diagram showing the ozone cleaning device along the A-A line of FIG. 1.

As shown in FIGS. 2 and 3, an ozone cleaning device according to a first embodiment of the present invention contains at least a conductive member 2, at least a reinforced casing member 1, at least a handle member 3, at least a power provision member 4, and at least a switch element 5. The conductive member 2 contains a metallic material and therefore is electrically conducting. The casing member 1 is injection-molded and houses the conductive member 2 inside in an airtight manner. The conductive member 2 is exposed from a bottom end of the casing member 1. The casing member 1 contains Polycarbonate (PC) for enhanced structural strength.

The bottom end of the casing member 1, together with the embedded conductive member 2, is joined to a top end of the handle member 3. The conductive member 2 is as such entirely prevented from exposure jointly by the casing member 1 and the handle member 3 for enhanced safety. The power provision member 4 is housed inside the handle member 3 and electrically connected to the conductive member 2 so that a high-voltage and low-current electrical power is fed to the conductive member 2 to avoid accidental electrical shock to a user of the ozone cleaning device. The switch element 5 is configured on the handle member 3 and electrically connected to the power provision member 4 to open or close its electrical path to the conductive member 2. What is described above is exemplary and the present invention is not limited as such.

Figure 4:
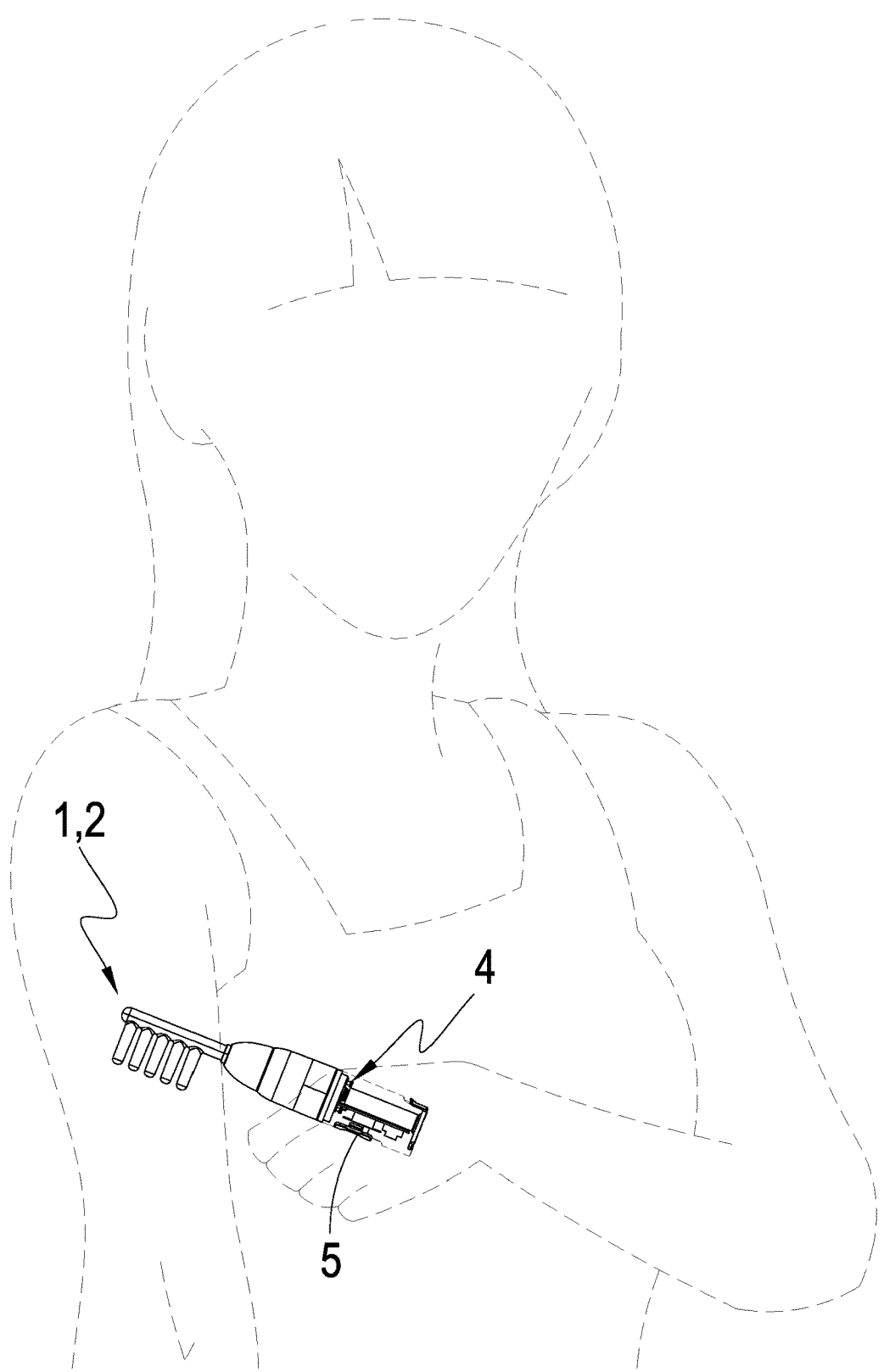
FIG. 4 is a schematic diagram showing the usage of the ozone cleaning device of FIG. 1.

As shown in FIGS. 2 to 4, the present invention achieves enhanced structural strength by tightly joining the casing member 1 and the conductive member 2 together so as to distribute external impact and to prevent the casing member 1 from being broken.

To use the ozone cleaning device, the ozone cleaning device is held close to a user and the switch element 5 is engaged so that the power provision member 4 delivers electricity to the conductive member 2. The conductive member 2 is then conducting to the user where the air in between is influenced by the electrical power to produce ozone for cleaning. Since high-voltage and low-current electricity is used, there is no harm to human body. If the casing member 1 is not close to a user, no zone would be produced even the switch element 5 is engaged. This will prevent the production of too much ozone when the switch element 5 is triggered accidentally.

Figure 5:
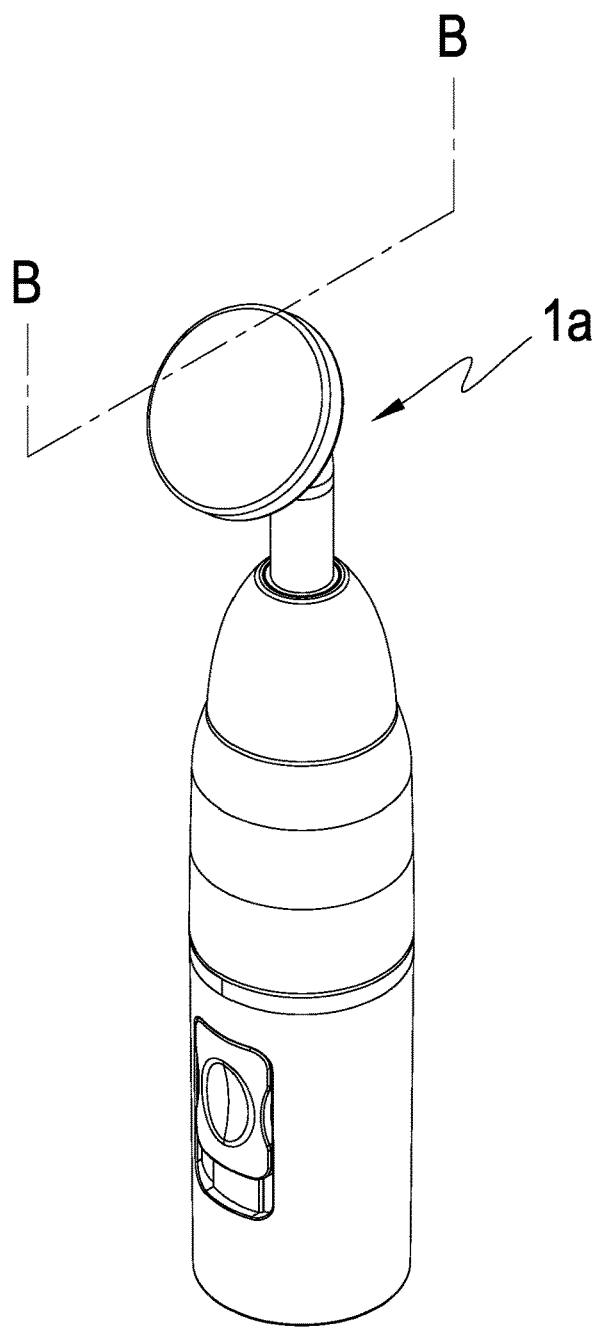
FIG. 5 is a perspective diagram showing an ozone cleaning device according to a second embodiment of the present invention.
Figure 6:
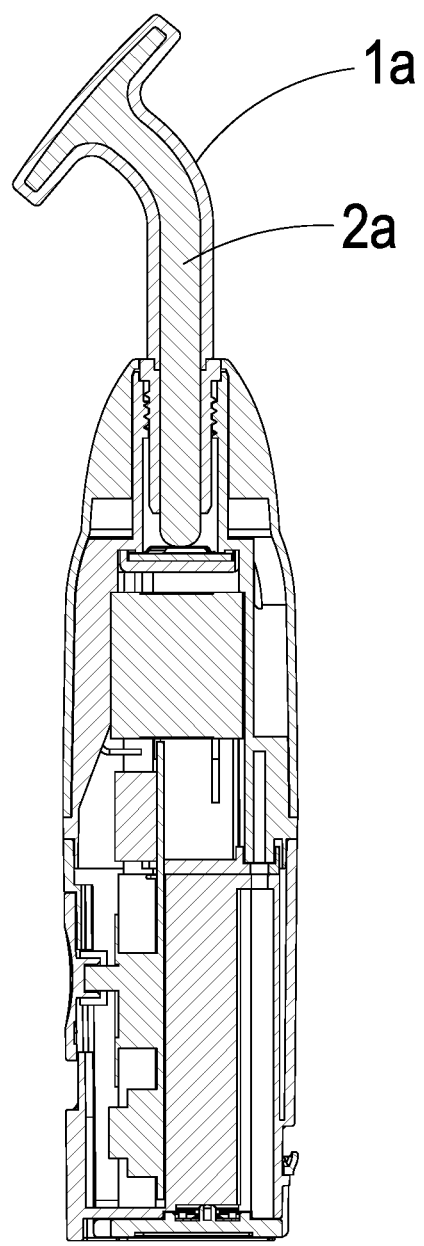
FIG. 6 is a sectional diagram showing the ozone cleaning device along the B-B line of FIG. 5.

As shown in FIGS. 5 and 6, a second embodiment of the present invention is different from the previous embodiment in that the conductive member 2a and the casing member 1a are of different shapes.

Therefore, the advantages of the present invention are as follows.

Firstly, the reinforcement of the casing member 1 achieves safe and convenient usage and transportation.

Secondly, the tight integration between the casing member 1 and the conductive member 2 further enhance the structural strength of the ozone cleaning device, thereby achieving prolonged operational life.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. An ozone cleaning device for a user comprising:
   an electrically conductive member;
   a casing member; and
   a handle member; wherein
   the casing member, together with the conductive member, is joined to a top end of the handle member;
   the casing member is injection-molded and houses the conductive member inside in an airtight manner;
   the conductive member is prevented from exposure jointly by the casing member and the handle member; and
   an electrical power is conducting through the conductive member and air between the user and the casing member is influenced by the electrical power to produce ozone.

2. The ozone cleaning device according to claim 1, wherein the casing member comprises Polycarbonate (PC) for enhanced structural strength.

3. The ozone cleaning device according to claim 1, further comprising a power provision member housed inside the handle member providing the electrical power to the conductive member.

4. The ozone cleaning device according to claim 3, further comprising a switch element configured on the handle member and electrically connected to the power provision member to open or close an electrical path between the power provision member and the conductive member.

5. The ozone cleaning device according to claim 3, wherein the power provision member delivers the electrical power to the conductive member.

6. The ozone cleaning device according to claim 1, where the conductive member comprises a metallic material.

* * * * *